United States Patent [19]

Machek et al.

[11] Patent Number: 4,834,112
[45] Date of Patent: May 30, 1989

[54] DEVICE FOR PRODUCING INCREMENTAL JOINT MOVEMENT IN A PATIENT

[75] Inventors: James E. Machek, Valencia; Edward J. Rhinehart, Monroeville, both of Pa.

[73] Assignee: Medrad, Inc., Pittsburgh, Pa.

[21] Appl. No.: 19,459

[22] Filed: Feb. 26, 1987

[51] Int. Cl.$^4$ .................................................. A61B 5/10
[52] U.S. Cl. .................................... 128/777; 128/20; 33/514
[58] Field of Search ................. 128/20, 774, 777, 782, 128/341–345; 33/143 R, 143 C, 143 M, 143 J, 143 K, 144, 511–515

[56] References Cited

U.S. PATENT DOCUMENTS

| | | | |
|---|---|---|---|
| 1,217,745 | 2/1917 | Gracey | 128/20 |
| 1,706,500 | 3/1920 | Smith | 128/20 |
| 1,823,045 | 9/1931 | Hommel | 33/143 J |
| 2,245,959 | 6/1941 | Brown | 33/143 J |
| 2,450,194 | 9/1948 | Glaser | 128/20 |
| 3,752,149 | 8/1973 | Ungar et al. | 128/20 X |
| 4,151,837 | 5/1979 | Millard, Jr. et al. | 128/20 X |
| 4,263,899 | 4/1981 | Burgin | 128/20 X |
| 4,337,762 | 7/1982 | Gauthier | 128/20 |
| 4,344,420 | 8/1982 | Forder | 128/20 |
| 4,469,108 | 9/1984 | Goldstein | 128/774 X |
| 4,606,128 | 9/1986 | Wyrwich et al. | 33/143 C |
| 4,627,421 | 12/1986 | Symbas et al. | 128/20 |

FOREIGN PATENT DOCUMENTS

1082417  3/1984  U.S.S.R. ........................ 128/341

Primary Examiner—Kyle L. Howell
Assistant Examiner—Angela D. Sykes
Attorney, Agent, or Firm—Fleit, Jacobson, Cohn & Price

[57] ABSTRACT

A device for providing precise incremental joint movement in a patient, includes first and second spaced retractors for engaging respective parts of the patient adjacent the joint. One of the retractors is mounted on a fixed support assembly and the other retractor is mounted on a movable actuation rod slidably mounted in the support assembly. The device is formed entirely on non-magnetic material and is readily operable by the patient, making the device especially useful in magnetic resonance imaging procedures. The retractors are of a construction such that they can be snapped onto the support assembly and the actuating rod, respectively, and then ruptured upon being removed therefrom, so as to prevent inadvertent use of the retractors on another patient. An operating mechanism for the actuating rod includes a handle-operable pawl, and a retaining mechanism for the actuating rod includes a spring-biased holding pawl, which can be pivoted to release the actuating rod so that it can be readily returned by hand by an initial closed position.

36 Claims, 3 Drawing Sheets

FIG. 2B

DEVICE FOR PRODUCING INCREMENTAL JOINT MOVEMENT IN A PATIENT

BACKGROUND OF THE INVENTION

1. Field of the Invention

This invention relates generally to a device for producing precise incremental joint movement in a patient, and more specifically to a device for producing precise temporalmandibular joint movement in a patient, wherein the device is operated by the patient during the making of internal images of the joint by magnetic resonance imaging.

2. Description of Related Art

It is known to diagnose various disorders, such as joint pain, by viewing internal images of the area under investigation at stepped positions. Such investigations can be performed by standard x-rays, by the new CT scan or by the even newer technique of magnetic resonance imaging (MRI).

For example, patients may suffer from a temporalmandibular joint (TMJ) disorder in which opening or closing of the lower jaw can be accomplished, if at all, only with severe pain or discomfort. Treating of these patients involves personal observation by a physician, which can be significantly advanced with the aid of a series of internal images made of the jaw area at spaced stages of jaw opening through MRI techniques.

In the past, the progressive opening of the temporalmandibular joint for the above diagnosis has been accomplished by the physician or a technician inserting a wedge-type dental block between the patient's jaw bones (i.e., teeth) and forcing the block rearward in "slow" incremental steps. A scissors-like forceps, having a releasable pawl mechanism for locking the forceps in each stage of jaw opening, also has been used.

The foregoing procedures have a number of disadvantages. For example, the use of the manually inserted wedge-type dental block is relatively inaccurate and requires the presence of the physician or technician with the patient for the insertion procedure. The scissors-like forceps, while more accurate, is cumbersome and unwieldy, and still requires great care for evenly-spaced steps.

Accordingly, a need exists for a device by which temporalmandibular joint incrementing in a magnetic resonance imaging procedure can be made precisely and simply without a physician or technician being in the immediate presence of the patient, and the primary purpose of this invention is to provide such a device.

SUMMARY OF THE INVENTION

In general, the invention relates to a device for precisely incrementing joint movement in a patient, which comprises first and second spaced retractors for engaging respective body parts of the patient adjacent the joint. The device further includes a support having the first retractor mounted on the support, and an actuating mechanism mounted on the support for movement relative thereto, with the actuating mechanism projecting from the support and having the second retractor mounted on the actuating mechanism adjacent the first retractor. An operating mechanism is provided on the support for causing a precise preselected incremental movement of the actuator mechanism and the second retractor for a single stroke of the operating mechanism, into successive incremented positions relative to the first retractor. A mechanism also is provided on the support for retaining the actuator mechanism and the second retractor in their incremented positions.

More specifically, the support is of elongated construction and the actuating mechanism is an elongated rod slidably mounted in the elongated support. The operating mechanism and the retaining mechanism each comprises a spring-biased pawl member engagable with respective teeth on the actuating rod. The operating mechanism includes a pivoted operating handle having the associated pawl member pivoted thereon, with a resilient-biasing mechanism disposed between the handle and the pawl member for holding the pawl member engaged with its respective teeth on the actuating rod. Another resilient-biasing mechanism is disposed between the support and the handle to bias the handle to an open position with respect to the support. Separate mechanisms are provided for adjusting the degree of pivotable movement of the handle and the position of the associated pawl thereon, to provide a precise desired movement of the first retractor for each pivoting of the handle.

Each of the retractors includes a body having a pair of spaced projecting clamping legs for mounting the retractor on a respective one of the elongated support or the elongated actuating rod, with at least one of the clamping legs being of resilient construction. A junction of at least one of the legs with the body is formed with a rupture line to provide a rupturable connection between the one leg and the body. Each of the retractors is mountable on the elongated support or the elongated actuating rod by sliding the spaced clamping legs thereon. At least one of the clamping legs includes a latch portion which then precludes removal of the retractor without pivoting the retractor about the support or the actuating rod, respectively, so that the leg is ruptured along the rupture line as the retractor is pivoted, whereby the retractor can not be re-used.

DETAILED DESCRIPTION

Figure 1:
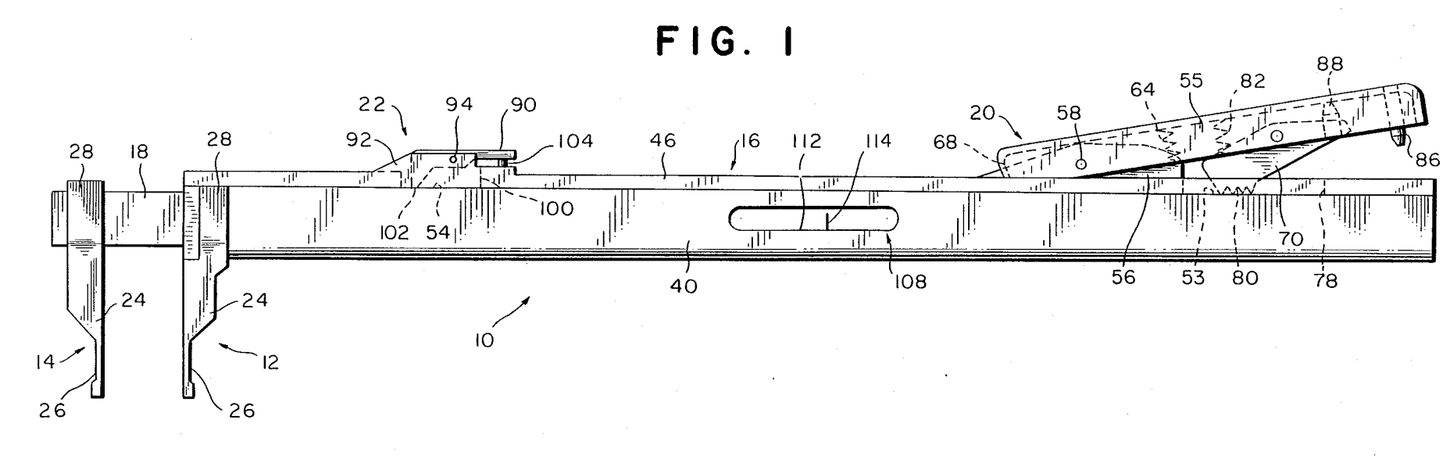
FIG. 1 is a schematic side view of a patient joint incrementing device in accordance with the invention.

In general, referring to FIG. 1, a temporalmandibular joint incrementing device 10 in accordance with the invention comprises first and second retractors 12 and 14, the first retractor being mounted on one end of a fixed support assembly 16 and the second retractor being mounted on a movable actuator rod 18 adjacent the first retractor. An actuator rod operating mechanism 20 is provided adjacent an opposite end of the support assembly 16 and a releasable actuator rod retaining mechanism 22 is provided on the support assembly adjacent the end of the support assembly at which the retractors 12 and 14 are located.

Figure 2A:
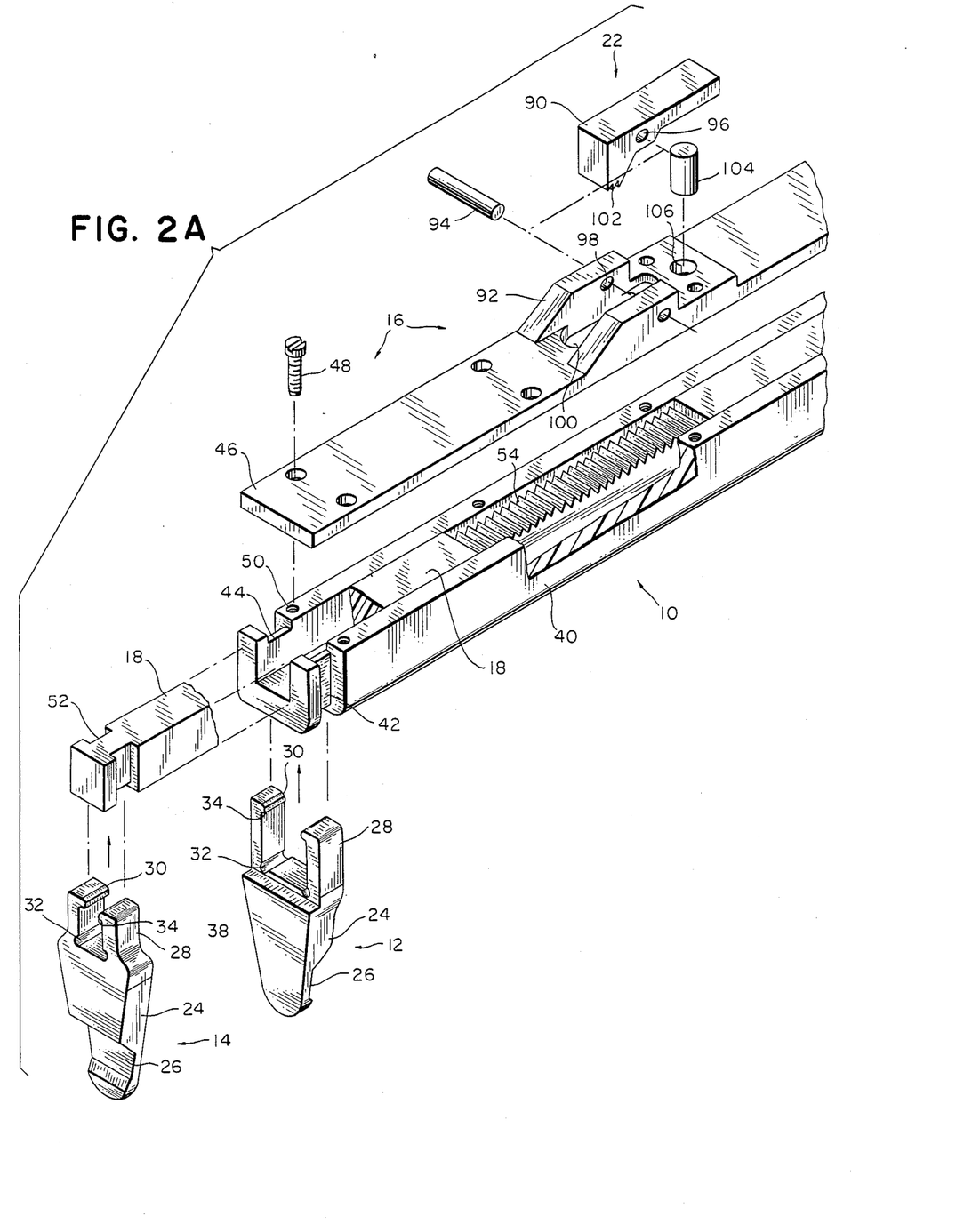
FIG. 2A is an isometric, partially exploded view of a part of the device shown in FIG. 1.

The retractors 12 and 14 are of similar construction, and therefore, only the first retractor will be described in detail, with like reference numbers in the drawings being used to designate like elements. As is best shown in FIG. 2A, the first retractor 12 includes a body 24 provided adjacent one end with a grooved flat seat portion 26 of substantial size to accommodate different "bites" of patients in use, and having a pair of spaced resilient clamping legs 28 extending from an opposite end. The spaced resilient clamping legs 28 permit the retractor 12 to be slidably mounted on the support assembly 16 in a linear direction, as illustrated by the arrow in FIG. 2A. For this purpose, an outer end of each leg 28 includes a tapered camming surface 30 for facilitating the mounting of the retractor 12 on the support assembly 16.

Figure 3:
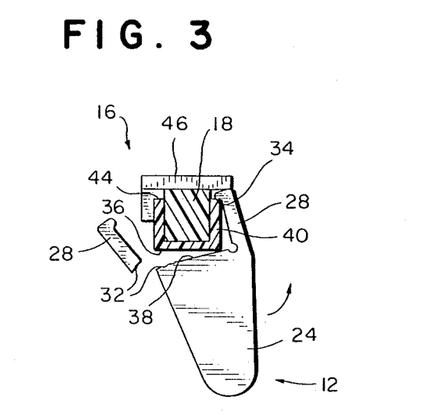
FIG. 3 is a schematic view illustrating a feature of the invention.

Each of the spaced resilient clamping legs 28, at a junction of the leg with the body 24, is provided with a groove 32 in the form of a three-quarter circle, or otherwise scored in a suitable manner, to define a rupture line and provide a rupturable connection between the leg and the body. The outer end of each leg 28 also includes an inner latching surface 34 for retaining the retractor 12 on the support assembly 16 during use. The latching surfaces 34 also prevent linear removal of the retractor 12 from the support assembly 16 after use; rather, to remove the retractor it must be pivoted about the longitudinal axis of the support assembly as illustrated in FIG. 3. This pivotable movement of the retractor 12 produces a camming force on one of the clamping legs 28 by an adjacent edge 36 of the support assembly 16, causing the clamping leg to break along the rupture line defined by the adjacent groove 32, as illustrated in FIG. 3. Thus, the retractor 12, having once been used, cannot be inadvertently re-used. The first retractor 12 also includes an abutment surface 38 (not on the second retractor 14) for seating the retractor on the support assembly 16.

Figure 2B:
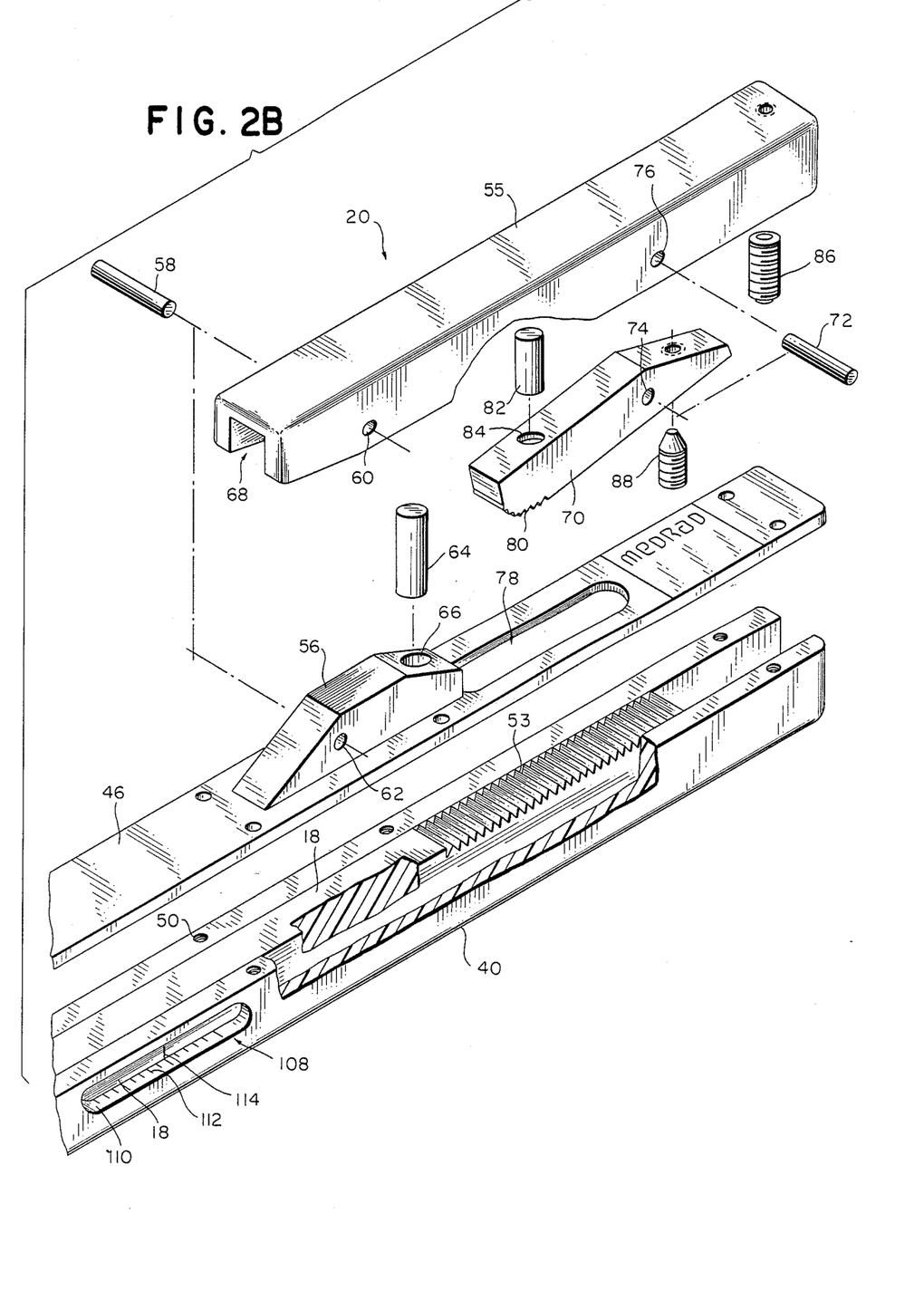
FIG. 2B is a continuation of the device shown in FIG. 2A and illustrating another part of the device.

As viewed in FIGS. 2A and 2B, the support assembly 16 comprises an elongated U-shaped channel member or housing 40 having a bottom and spaced upstanding side legs. The left-hand end of the housing 40, as viewed in FIG. 2A, is provided with a U-shaped slot 42, for receiving the spaced clamping legs 28 of the first retractor 12. Adjacent an upper end, the U-shaped slot 42 is provided with upwardly facing surfaces 44 engagable by the latch surfaces 34 of the first retractor legs 28, for retaining the retractor on the housing 40.

As is clearly shown in FIG. 2A, the support assembly 16 further includes a cover plate 46 which is secured to the upper ends of the side legs of the U-shaped member or housing 40 by suitable screws 48 (only one shown) receivable in screw-threaded holes 50, and which extends between the upper ends to confine the rod in the member or housing 40 for longitudinal movement. The cover plate 46 has the actuating rod operating mechanism 20 (FIG. 2B) and the actuating rod retaining mechanism 22 (FIG. 2A) mounted thereon.

The actuating rod 18 is mounted for slidable movement in a channel defined by the U-shaped housing 40 and the cover plate 46, as best illustrated in FIGS. 2A and 2B. At its left hand end, as viewed in FIG. 2A, the actuating rod 18 is provided with a pair of vertical slots 52 on opposite sides thereof for receiving the spaced resilient clamping legs 28 of the movable second retractor 14. When the second retractor 14 is assembled on the actuating rod 18, the latch surfaces 34 of the retractor clamping legs 28 engage with upper surface portions of the actuating rod adjacent the slots 52, to preclude removal of the retractor from the actuating rod except by pivoting the retractor about the longitudinal axis of the actuating rod and causing rupturing of one of the clamping legs, as described above for the first retractor 12 and illustrated in FIG. 3.

The actuating rod operating mechanism 20 includes an operating handle 55 of inverted essentially U-shaped construction having a top portion and depending side legs. One end of the operating handle 55 straddles and is pivotably mounted on a wedge-shaped support 56, which is integral with the cover plate 46, by a pivot pin 58 received in aligned apertures 60 and 62 in the handle and the wedge-shaped support, respectively. The operating handle is biased counter-clockwise, as viewed in FIG. 2B, to an open position with respect to the cover plate 46, by a spring 64 disposed at a lower end in a circular seat 66 in the cover plate wedge-shaped support 56 and engaged at its upper end with the inside of the top portion of the handle. At its left-hand end, as viewed in FIG. 2B, the handle 55 also includes a slot 68 which straddles the wedge-shaped support 56 when the handle is in the open position.

The actuating rod operating mechanism 20 further includes a pusher pawl 70 pivotably mounted on the operating handle 55 by a pivot pin 72 extended through aligned apertures 74 and 76 in the pusher pawl and the side legs of the handle, respectively. A left-hand end of the pusher pawl 70, as viewed in FIG. 2B, is disposed in an elongated slot 78 in the cover plate 46 and has pusher teeth 80 on its underside engaged with the teeth 53 on the upper surface of the actuating rod 18. The pusher teeth 80 on the pawl 70 are retained in engagement with the teeth 53 on the actuating rod 18 by a spring 82 disposed at its lower end in a circular seat 84 in the pawl and engaged at its upper end with an undersurface of the top portion of the handle 55.

A first set screw 86 is screw threadably mounted in the top portion of the handle 55 and has a lower end engagable with the cover plate 46 to limit pivotable movement of the handle toward the cover plate. A second set screw 88 is screw threadably mounted in the pusher pawl 70 and has an upper end engagable with the undersurface of the top portion of the handle 55, for adjusting the position of the teeth 80 of the pusher pawl with respect to the teeth 53 in the actuating rod 18 to compensate for slight errors in the fabrication of the teeth and assure a proper mesh therebetween. Thus, by appropriate adjustment of the set screws 86 and 88, the stroke of the pusher pawl 70 in response to each pivoting of the handle 55 can be set to produce a precise incremental stroke of the second retractor 14 of a preselected value, such as 1 mm.

Referring to FIG. 2A, the actuating rod retaining mechanism 22 includes a holding pawl 90 mounted for pivotable movement between a pair of spaced upstanding pawl supports 92 integrally formed with the cover plate 46, by means of a pivot pin 94 extending through aligned apertures 96 and 98 in the holding pawl and the pawl supports. A left-hand end portion (as viewed in FIG. 2A) of the holding pawl 90 is received in an elongated slot 100 in the cover plate 46 between the pawl supports 92, and is provided on an underside thereof with retaining teeth 102 engaged with the retaining teeth 54 in the upper surface of the actuating rod 18. The pawl-retaining teeth 102 are releasably held in engagement with the retaining teeth 54 by a spring 104 having a lower end disposed in a circular seat 106 in the cover plate 46 and having an upper end engaged with an underside of the holding pawl. Thus, as long as the holding pawl teeth 102 are engaged with the teeth 54 in the actuating rod 18, retrograde movement of the actuating rod (to the right in FIGS. 2A and 2B) is precluded; however, upon manually pivoting the holding pawl 90 against the action of its biasing spring 104 to release the pawl teeth 102 from the teeth 54 in the actuating rod 18, the actuating rod can be moved manually to the right in FIGS. 2A and 2B, to a closed or collapsed position with respect to the support assembly 16.

As is shown in FIG. 2B, the device also may be provided with a scale 108 for the purpose of indicating the number of incremental advances which has occurred at any particular time. The scale 108 includes an elongated slot 110 formed in one of the side legs of the U-shaped housing 40, and provided with a series of gradations 112 spaced, for example, 1 mm. apart, and numbered to represent the number of incremental advances of the actuating rod made in response to operation of the operating mechanism 20. Similarly, a reference line is provided on the actuating rod 18 so that as the actuating rod is advanced, the reference line moves with respect to the gradations 112 on the housing 40 to give an indication as to the amount which the actuating rod has moved.

Figure 4:
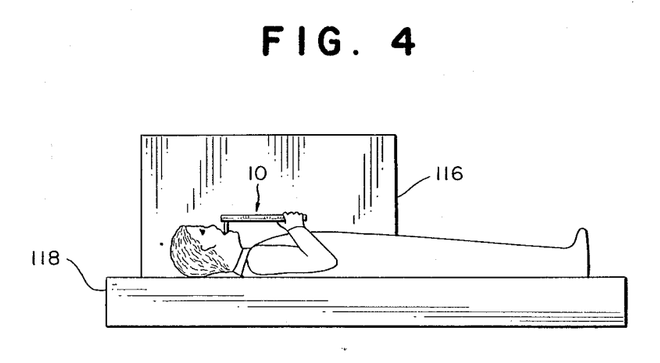
FIG. 4 is a schematic view of a patient utilizing the device in accordance with the invention.

FIG. 4 illustrates one manner of using the incrementing device 10 in accordance with the invention, in conjunction with a magnetic resonance imaging system 116, for producing internal images of a temporalmandibular joint of a patient for diagnostic purposes. With the patient lying in a prone position on a support table 118 of the magnetic resonance imaging system 116, and with the movable retractor 14 in a zero position, the retractors 12 and 14 are positioned in the patient's mouth with the seats 26 of the retractors engaging respective ones of the patient's front teeth. The patient then holds the device 10 in one hand so as to be capable of pivoting the operating handle 55, and the imaging procedure is ready to begin. During the imaging procedure, the technician performing the procedure is located in another room at a control panel for the magnetic resonance imaging system 116.

A the beginning of the imaging procedure, the patient is told by the technician, as for example, through a speaker in the magnetic resonance imaging room, to click the device 10 one time. The patient then pivots the operating handle 55 a full stroke to cause advancement of the actuating rod 18 one increment, causing the retaining pawl 90 to be pivoted and then to snap into the next adjacent tooth 54 in the actuating rod with a loud "click". The technician then actuates the magnetic resonance imaging system 116 to produce a series of still images of the temporalmandibular joint of the patient. If necessary, a microphone may be provided in the vicinity of the patient and connected to a speaker in the control room, to assist the technician in hearing the clicking of the device 10 as it is actuated by the patient. After the first series of images has been completed, the technician advises the patient to operate the device 10 again, whereupon a second series of images is produced. This procedure is continued until the desired incrementing of the temporalmandibular joint and the desired number of images has been produced. If during the imaging procedure, the patient experiences pain or discomfort upon any specific incrementing step, the patient can signal to the technician, who then will make an indication of this fact by recording the increment advance number of the device at which the pain or discomfort was experienced.

Since the device 10 is intended to be used in a magnetic system, the device is formed entirely of non-magnetic material. For example, the springs 64, 82 and 104 may be formed in the shape of cylinders from an elastomer silastic material, and the remainder of the device 10 may be formed of a hard, biocompatible plastic, such as a polycarbonate, or a plastic sold under the tradename Delrin or Nylon.

While the device 10 has been disclosed in conjunction with the producing of internal images of a temporalmandibular joint, with the device being operated by the patient, it is contemplated that the device also could be used for other purposes and in other manners. For example, rather than adjusting the pawl member 90 to produce one click for each increment of the actuating rod 18, the pawl member could be adjusted to produce more than one click upon each operation of the actuating rod. The device 10 also could be used in a therapeutic manner, as for example, where a physician wants a patient to open the lower jaw to a precise amount each day after having oral surgery, e.g., six clicks for two days, then ten clicks for two days, etc. The principles of the device 10 also could be used for other diagnostic imaging procedures in a magnetic resonance imaging room, such as incremental positioning of a shoulder, knee, etc. It is also contemplated that instead of being manually operated, the device could be remote controlled by air, etc.

In summary, a new and improved device 10 for producing precise incremental movement in a joint of a patient, such as a temporalmandibular joint, has been disclosed. The device 10 is operable by the patient without the immediate presence of a technician, thus making the device especially suitable in magnetic resonance imaging procedures. The device includes snap-on retractors 12 and 14, which automatically become broken upon pivotable removal of the retractors from the U-shaped housing 40 and the actuating rod 18, respectively, so that the retractors cannot be inadvertently re-used with another patient.

It should be appreciated that the preceding description has been for the purpose of illustration only, and is in no way intended to be limiting. Rather, it is the intention that the present invention be limited only as defined in the appended claims.

What is claimed is:

1. A device for producing precise incremental joint movement in a patient, which is adapted to be operable by one hand of a user and which comprises:
    first and second spaced retractors for engaging respective body parts of the patient adjacent the joint;
    support means having said first and second retractors mounted thereon for relative movement, said support means comprising a holder portion by which the device is adapted to be held by a user operating the device;
    actuating means mounted on said support means for movement relative to said support means, said actuating means being movable to cause relative movement between said first and second retractors;
    operating means movably mounted on said support means for causing a precise preselected incremental movement of said actuating means for a single stroke of said operating means, to cause relative movement between said first and second retractors into successive incremented positions relative to said support means and one another, said operating means being located adjacent said holder portion so that said holder portion and said operating means both can be grasped in one hand of the user and said operating means can be moved by the user on each stroke thereof from an initial position toward said holder portion to cause the precise incremental movement of said actuating means to cause the relative movement between said first and second retractors; and means on said support means for retaining said actuating means and said first and second retractors in their relative incremented positions.

2. The device as in claim 1, wherein said device is formed entirely of non-magnetic material.

3. The device as in claim 1 wherein:

resilient means is provided for returning said operating means back to its initial position after each operation of said operating means; and said operating means comprises a pawl member engageable with teeth on said actuating means to precisely increment said actuating means and said second retractor on each stroke of said operating means, said pawl member being movable relative to said teeth as said operating means is moved back to its initial position by said resilient means.

4. The device as in claim 3, wherein said retaining means comprises a releasable pawl resiliently biased into engagement with additional teeth on said actuating means.

5. The device as in claim 1, wherein:

resilient biasing means is provided for returning said operating means back to its initial position after each operation of said operating means.

6. The device as in claim 1, wherein:

said device is adapted to be used with said retractors engaged with a patient's teeth in respective jaws of the patient; and said retractors include respective grooves having flat elongated bottom surfaces which are parallel to one another and which face in opposite directions away from one another, for accommodating the patient's bite.

7. The device as in claim 1, wherein said operating means comprises:

a pawl member engageable with teeth on said actuating means;

first resilient means for holding said pawl member engaged with the teeth on said actuating means; and second resilient means for returning said operating means to the initial position of said operating means.

8. The device as in claim 7, further comprising:

means for adjusting the degree of movement of said operating means on said support means, and the position of said pawl member relative to the teeth on said actuating means.

9. The device as in claim 8, wherein said adjusting means includes first and second screws disposed, respectively, between said support means and said operating means, and between said pawl member and said actuating means.

10. The device as in claim 1, wherein at least one of said retractors includes a pair of spaced parallel clamping legs mounting said one retractor on either said support means or said actuating means, with said clamping legs having outer free ends and at least one of said clamping legs being of resilient construction.

11. The device as in claim 10, wherein:

said at least one retractor includes a body having said clamping legs projecting from said body, with said body being provided with a rupture line at a junction between at least one of said legs and said body, to provide a rupturable connection between said latter leg and said body.

12. The device as in claim 11, wherein:

said at least one retractor is mountable on said support means or said actuating means by sliding said spaced clamping legs onto said support means or said actuating means in a direction extending parallel to said legs;

said support means or said actuating means, and at least one of said legs of said at least one retractor, includes means for precluding removal of said one retractor from said support means or said actuating means except by pivoting said one retractor about said support means or said actuating means; and said support means or said actuating means includes means for causing rupturing of the rupturable connection at said at least one leg-body junction as said one retractor is pivoted about said support means or said actuating means, to render said one retractor unfit for re-use.

13. The device as in claim 12, wherein:

said retractor removal precluding means on said support means or said actuating means comprises at least one groove for receiving one of said legs of said at least one retractor; and said retractor removal precluding means on said at least one retractor comprises latch means on at least one of the legs of said one retractor.

14. The device as in claim 1, further comprising scale indicator means formed at least in part on said actuating means for indicating the number and the amount of the incremental movements of said actuating means relative to said support means.

15. A retractor for use in a device for producing precise incremental joint movement in a patient, which comprises:

a body; and a pair of spaced parallel legs projecting from said body, said spaced legs having outer free ends for receiving a portion of the device therebetween and slidably mounting the retractor on the device in a direction extending parallel to said spaced legs, with at least one of said legs being of resilient construction; and at least one of said legs having a junction with said body which includes a rupture line to provide a rupturable connection between said leg and said body.

16. The retractor as in claim 15 wherein:

at least one of said legs includes cam means at the outer free end thereof for biasing said legs apart as said retractor is slidably mounted on the device; and at least one of said legs includes latch means at the outer free end thereof for precluding removal of said retractor from the device after use except by pivoting said retractor about a portion of the device and causing rupturing of the rupturable connection at said at least one leg-body junction, to render said retractor unfit for re-use.

17. A device for producing precise incremental joint movement in a patient, which comprises:

first and second spaced retractors for engaging respective body parts of the patient adjacent the joint;

support means having said first retractor mounted thereof, said support means being of elongated construction and including a U-shaped member and a cover plate;

actuating means mounted on said support means for movement relative to said support means, said actuating means including an elongated rod slidably mounted on said support means in said U-shaped member and cover plate with said rod projecting from said support means and having said second retractor mounted on said rod adjacent said first retractor;

operating means on said support means for causing a precise preselected incremental movement of said rod and said second retractor for a single stroke of said operating means, to move said second retractor into successive incremented positions relative to said support means and said first retractor; and means on said support means for retaining said rod and said second retractor in their incremented positions.

18. The device as in claim 17 wherein said retaining means comprises a releasable pawl member resiliently biased into engagement with additional respective teeth on said actuating means.

19. The device as in claim 17, further comprising scale indicator means formed in part on said support means and in part on said actuating rod, for indicating the number and the amount of the incremental movements of said actuating rod relative to said support means.

20. A device for producing precise incremental joint movement in a patient, which comprises:

first and second spaced retractors for engaging respective body parts of the patient adjacent the joint;

support means having said first retractor mounted thereon, said support means comprising a holder portion by which the device is adapted to be held by a user operating the device;

actuating means mounted on said support means for movement relative to said support means, said actuating means projecting from said support means and having said second retractor mounted on said actuating means adjacent said first retractor;

operating means on said support means for causing a precise preselected incremental movement of said actuating means and said second retractor for a single stroke of said operating means, to move said second retractor into successive incremented positions relative to said support means and said first retractor;

said operating means comprising a pawl member engageable with teeth on said actuating means to precisely increment said actuating means and said second retractor on each stroke of said operating means, said pawl member being movable relative to said teeth as said operating means moves back to its initial position;

said operating means further comprising an operating handle pivotably mounted on said support means adjacent said holder portion and movable by the user on each stroke thereof from an initial position toward said holder portion to cause the precise incremental movement of said actuating means and said second retractor relative to said support means and said first retractor, said pawl member being pivotably mounted on said handle;

first resilient means disposed between said handle and said pawl member for holding said pawl member engaged with the teeth on said actuating means;

second resilient means disposed between said support means and said handle for biasing said handle to the open initial position with respect to said support means; and means on said support means for retaining said actuating means and said second retractor in their incremented positions.

21. The device as in claim 20, further comprising:

means for adjusting the degree of pivotable movement of said handle on said support means, and the position of said pawl member relative to the teeth on said actuating means.

22. The device as in claim 21, wherein said adjusting means includes first and second screws disposed, respectively, between said support means and said handle, and between said pawl member and said actuating means.

23. The device as in claim 20, wherein:

said retaining means comprises a releasable pawl resiliently biased into engagement with additional respective teeth on said actuating means;

each of said retractors includes a pair of spaced clamping legs mounting said retractor on a respective one of said support means or said actuating means, with at least one of said clamping legs being of resilient construction;

each of said retractors includes a body having said clamping legs projecting from said body, and said body being provided with a rupture line at a junction between at least one of said legs and said body to provide a rupturable connection between said latter leg and said body;

each of said retractors is mountable on said support means or said actuating means by sliding said spaced clamping legs onto said support means or said actuating means;

each of said support means and said actuating means, and at least one of said legs of each of said retractors, includes means for precluding removal of said retractor from said support means or said actuating means except by pivoting said retractor about said support means or said actuating means; and said support means and said actuating means each include means for causing rupturing of the rupturable connection at said at least one leg-body junction as said retractor is pivoted about said support means or said actuating means, to render said retractor unfit for re-use.

24. A device for producing precise incremental joint movement in a patient, which comprises:

first and second spaced retractors for engaging respective body parts of the patient adjacent the joint;

support means having said first retractor mounted thereon;

actuating means mounted on said support means for movement relative to said support means, said actuating means projecting from said support means and having said second retractor mounted on said actuating means adjacent said first retractor;

each of said retractors including a pair of spaced parallel clamping legs mounting said retractor on a respective one of said support means and said actuating means, with said clamping legs having outer free ends and at least one of said clamping legs of each retractor being of resilient construction;

operating means on said support means for causing a precise preselected incremental movement of said actuating means and said second retractor for a single stroke of said operating means, to move said second retractor into successive incremented positions relative to said support means and said first retractor; and means on said support means for retaining said actuating means and said second retractor in their incremented positions.

25. The device as in claim 24, wherein:

each of said retractors includes a body having said clamping legs projecting from said body, with said body being provided with a rupture line at a junction between at least one of said legs and said body, to provide a rupturable connection between said latter leg and said body.

26. The device as in claim 25, wherein:

each of said retractors is mountable on respective ones of said support means and said actuating means by sliding said spaced clamping legs onto said support means or said actuating means in a direction extending parallel to said legs;

each of said support means and said actuating means, and at least one of said legs of each of said retractors, includes means for precluding removal of said retractor from said support means or said actuating means except by pivoting said retractor about said support means or said actuating means; and said support means and said actuating means include means for causing rupturing of the rupturable connection at said at least one leg-body junction as said retractor is pivoted about said support means or said actuating means, to render said retractor unfit for re-use.

27. The device as in claim 26, wherein:

said retractor removal precluding means on said support means and said actuating means comprises at least one groove for receiving one of said legs of each retractor; and said retractor removal precluding means on each retractor comprises latch means on at least one of the legs of said retractor.

28. A device for producing precise incremental joint movement in a patient, which comprises:

first and second spaced retractors for engaging respective body parts of the patient adjacent the joint;

support means having said first retractor mounted thereon, said support means being of elongated construction and including a U-shaped member having spaced side legs and a rod-confining means extending at least partially between ends of said legs;

actuating means mounted on said support means for movement relative to said support means, said actuating means including an elongated rod slidably mounted on said support means for longitudinal movement in said U-shaped member and said rod-confining means, with said rod having said second retractor mounted on said rod adjacent said first retractor;

operating means on said support means for causing a precise preselected incremental movement of said rod and said second retractor for a single stroke of said operating means, to move said second retractor into successive incremented positions relative to said support means and said first retractor; and means on said support means for retaining said rod and said second retractor in their incremented positions.

29. The device as in claim 28, further comprising scale indicator means formed at least in part on said actuating rod, for indicating the number and the amount of the incremental movements of said actuating rod relative to said support means.

30. The device as in claim 28 wherein:

said retaining means comprises a releasable pawl resiliently biased into engagement with additional respective teeth on said actuating means;

at least one of said retractors includes a pair of spaced clamping legs mounting said retractor on at least one of said support means or said actuating means, with at least one of said clamping legs being of resilient construction;

said at least one retractor includes a body having said clamping legs projecting from said body, and said body being provided with a rupture line at a junction between at least one of said legs and said body to provide a rupturable connection between said latter leg and said body;

said at least one retractor is mountable on said support means or said actuating means by sliding said spaced clamping legs onto said support means or said actuating means;

said support means or said actuating means, and at least one of said legs of said one retractor, include means for precluding removal of said one retractor from said support means or said actuating means except by pivoting said one retractor about said support means or said actuating means; and said support means or said actuating means includes means for causing rupturing of the rupturable connection at said at least one leg-body junction as said one retractor is pivoted about said support means or said actuating means, to render said one retractor unfit for re-use.

31. A device for producing precise incremental joint movement in a patient, comprises:

first and second spaced retractors for engaging respective body parts of the patient adjacent the joint;

support means having said first retractor mounted thereon, said support means comprising a holder portion by which the device is adapted to be held by a user operating the device;

actuating means mounted on said support means for movement relative to said support means, said actuating means having said second retractor mounted on said actuating means adjacent said first retractor;

operating means on said support means for causing a precise preselected incremental movement of said actuating means and said second retractor for a single stroke of said operating means, to move said second retractor into successive incremented positions relative to said support means and said first retractor;

said operating means comprising a pawl member engageable with teeth on said actuating means to precisely increment said actuating means and said second retractor on each stroke of said operating means, said pawl member being movable relative to said teeth as said operating means moves back to its initial position;

said operating means further comprising an operating handle pivotably mounted on said support means adjacent said holder portion and movable by the user on each stroke thereof from an initial position toward said holder portion to cause the precise incremental movement of said actuating means and said second retractor relative to said support means and said first retractor, said pawl member being mounted on said handle;

resilient means disposed between said support means and said handle for biasing said handle to the open initial position with respect to said support means; and means on said support means for retaining said actuating means and said second retractor in their incremented positions.

32. The device as in claim 31, wherein said retaining means comprises a releasable pawl member resiliently biased into engagement with additional teeth on said actuating means.

33. A device for producing precise incremental joint movement in a patient, which comprises:

first and second spaced retractors for engaging respective body parts of the patient adjacent the joint;

support means having said first retractor mounted thereon;

actuating means mounted on said support means for movement relative to said support means, said actuating means having said second retractor mounted on said actuating means adjacent said first retractor;

at least one of said retractors including a pair of spaced parallel clamping legs mounting said one retractor on at least one of said support means or said actuating means, with said clamping legs having outer free ends and at least one of said clamping legs of said one retractor being of resilient construction;

operating means on said support means for causing a precise preselected incremental movement of said actuating means and said second retractor for a single stroke of said operating means, to move said second retractor into successive incremented positions relative to said support means and said first retractor; and means on said support means for retaining said actuating means and said second retractor in their incremented positions.

34. The device as in claim 33, wherein:

said one retractor includes a body having said clamping legs projecting from said body, with said body being provided with a rupture line at a junction between at least one of said legs and said body, to provide a rupturable connection between said latter leg and said body.

35. The device as in claim 34, wherein:

said one retractor is mountable on the at least one of said support means or said actuating means by sliding said spaced clamping legs onto said support means or said actuating means in a direction extending parallel to said legs;

said support means or said actuating means, and at least one of said legs of said one retractor, include means for precluding removal of said retractor from said support means or said actuating means except by pivoting said one retractor about said support means or said actuating means; and said support means or said actuating means includes means for causing rupturing of the rupturable connection at said at least one leg-body junction as said one retractor is pivoted about said support means or said actuating means, to render said one retractor unfit for re-use.

36. The device as in claim 35, wherein:

said retractor removal precluding means on said support means or said actuating means comprises at least one groove for receiving one of said legs of said one retractor; and said retractor removal precluding means on said one retractor comprises latch means on at least one of the legs of said one retractor.

* * * * *